(12) United States Patent
Larcher et al.

(10) Patent No.: US 9,783,768 B2
(45) Date of Patent: Oct. 10, 2017

(54) AUTOMATED CELL CULTURE SYSTEM

(75) Inventors: Yves Larcher, Schlieren (CH); Rupert Hagg, Wittenbach (CH)

(73) Assignee: Octane Biotech, Inc., Kingston (CA)

( * ) Notice: Subject to any disclaimer, the term of this patent is extended or adjusted under 35 U.S.C. 154(b) by 0 days.

(21) Appl. No.: 13/642,269

(22) PCT Filed: Apr. 20, 2011

(86) PCT No.: PCT/CH2011/000088
§ 371 (c)(1),
(2), (4) Date: Jan. 28, 2013

(87) PCT Pub. No.: WO2011/130865
PCT Pub. Date: Oct. 27, 2011

(65) Prior Publication Data
US 2013/0210130 A1    Aug. 15, 2013

Related U.S. Application Data

(60) Provisional application No. 61/326,532, filed on Apr. 21, 2010.

(51) Int. Cl.
| C12M 1/00 | (2006.01) |
| C12M 3/00 | (2006.01) |
| C12M 1/26 | (2006.01) |
| C12M 1/34 | (2006.01) |
| C12M 1/36 | (2006.01) |

(52) U.S. Cl.
CPC ............ *C12M 21/00* (2013.01); *C12M 23/44* (2013.01); *C12M 23/48* (2013.01); *C12M 23/50* (2013.01); *C12M 33/10* (2013.01); *C12M 41/14* (2013.01); *C12M 41/36* (2013.01); *C12M 41/48* (2013.01)

(58) Field of Classification Search
CPC ...... C12M 23/44; C12M 21/00; C12M 23/48; C12M 23/50; C12M 33/10; C12M 41/14; C12M 41/36; C12M 41/48
USPC .......................................... 435/286.2, 287.2
See application file for complete search history.

*Primary Examiner* — Nathan Bowers
*Assistant Examiner* — Lydia Edwards
(74) *Attorney, Agent, or Firm* — Shumaker, Loop & Kendrick, LLP

(57) ABSTRACT

The automated cell culture arrangement according to the invention comprises at least one closed cell culture module with at least one bioreactor. The closed cell culture module is a closed system, which means that within the closed cell culture module a closed sterile environment can be maintained. The automated cell culture arrangement according to the invention, further comprises at least one pump for pumping liquids within the closed cell culture module and at least one additional tool module, which is configured or configurable to act upon or to monitor the contents of a bioreactor and is movable relative to the at least one closed cell culture module or it is movable relative to one or several components of the at least one closed cell culture module.

18 Claims, 9 Drawing Sheets

AUTOMATED CELL CULTURE SYSTEM

RELATED APPLICATIONS

This application is a U.S. National Phase which corresponds to PCT International Application No. PCT/CH2011/000088, filed Apr. 20, 2011, which claims the benefit of U.S. Provisional Patent Application Ser. No. 61/326,532, filed Apr. 21, 2010. The subject matter of the aforementioned applications is incorporated herein by references in their entireties.

FIELD OF THE INVENTION

The invention lies in the field of biotechnology, in particular cell culture technology and bio-manufacturing technology. The invention particularly relates to the production of cell based or cell-derived-medical therapeutics including tissue engineering and cells for therapy.

BACKGROUND OF THE INVENTION

Since the cultivation of cells ex vivo was discovered in the early twentieth century cell culture has matured from a simple, microscope driven, observational science to a universally acknowledged technology with roots, which are set as deep in academia as they are in industry. Recent advances in cell therapies and tissue engineering are paving the road to regenerative medicine. The goals of this field include replacing, repairing and regenerating tissues and organs. Furthermore, medical treatment with cell-based products and procedures often lead to better therapeutic results than available pharmaceutical drugs or medical devices.

Today cells of many human tissues can be cultured ex vivo. Numerous biotechnology companies have been pursuing projects over more than ten years to commercialize cell-based products on a fee-for-service basis; however, most with very limited success. Among the hurdles are the high costs associated with Good-Manufacturing-Practice compliant manufacturing. Notably, manufacturing of innovative cellular therapeutics is still generally dependent on manual operation and manual control of traditional cultivation systems.

Partially automated bioreactor systems have been developed typically for the production of high density cultures of a single cell type often used with automatically regulated medium flow, oxygen delivery, temperature control. In such bioreactors once the cell culture was set up, the process runs with little manual intervention, thus limiting sources of contamination of the cell culture; yet, the set-up, process monitoring and harvesting procedures are still performed manually. However, there is also a demand for more complex cell culture processes yielding three-dimensional cell tissues and or multiple cell types grown in one cell culture.

EP 0,832,182 describes an improved bio-manufacturing system termed Replicell-System by Aastrom Biosciences. The Replicell-System is a modular system for automated cell expansion over a fixed time period comprising a cell processor, a system manager, individual incubator units, as well as patient-specific disposable cultivation cassettes with electronic application keys. Advantages of this system is the relatively high degree of automation with respect to proliferation of bone marrow derived cells if compared with manual proliferation of such cells over one or more passages using traditional T-flask approaches. Once initial cell seeding within the proliferation bioreactor is done, the following cell growth in a closed Replicell bioreactor system over a pre-defined cultivation period including media exchange is achieved in a largely automated manner. One major disadvantage of the system, however, is its limited flexibility. The Replicell automated cell manufacturing system is very much tailored to Aastrom's patented "single-pass perfusion" cell culture technology for stem cell and hematopoietic cells production as described in U.S. Pat. No. 5,763,266. Human stem and/or hematopoietic cells are grown to large quantities over one passage, only. The Replicell system, designed for this purpose, provides the combination of appropriate bioreactors and the execution of subtle single passage cell culture protocols with appropriate levels of nutrients and growth factors while simultaneously removing undesirable metabolic products. In contrast, the majority of cell-based and cell-derived medical therapeutics still require protocols with multiple passages, where an initial small number of cells is being expanded over several passages. The Replicell-System is not flexible enough to allow expansion of cells over more than one passage. Further, even for this single-passage-only cell culture protocol the Replicell system exhibits a very complex but still only partially automated mechanism to achieve proliferation of cells: Two different and independent devices are required for automated handling of cell proliferation whereas the transition from one device to the other still demands manual skill and handling. Furthermore, the continuous monitoring of critical cell growth parameters such as pH and O2 by means of biosensors is not possible with the Replicell-System, and most importantly this manufacturing system does not provide such important bioprocessing steps as biopsy digest, cell wash, cell concentration, and cell differentiation.

WO 03087292 and WO 05116186 describe a tissue engineering system termed ACTES system from Millenium Biologix. The ACTES system has been designed to include a wider set of linked bioreactor and other system compartments to address a variety of bio-processing events such as biopsy digest, cell proliferation, cell wash and cell collection as well as the differentiation, including thus the possibility for de novo tissue formation. Also the possibility of monitoring cell cultivation parameters such as pH and O2 during processing has been integrated allowing a constant monitoring over the cultivation process. However, despite enabling the automation of several cultivation processes, the ACTES system like the Replicell system provides only one cell growth chamber with a pre-defined size/volume ratio. As a consequence the ACTES system, too, is tailored to only very few highly specific applications, such as the production of cartilage tissue from a small number of cells obtained from a cartilage biopsy. For successful cartilage tissue production using the ACTES System it is even required to have access to a proprietary growth factor cocktail (U.S. Pat. No. 6,582,960 entitled "Use of fibroblast growth factor 2 for expansion of chondrocytes and tissue engineering").

Thus, it is the object of the current invention to provide an automated cell culture arrangement using a closed system approach, which is suited for a wide variety of cell culture protocols. In particular, it is an object of the invention to provide an automated cell culture arrangement, for which standard established manual cell culture protocols can be adapted easily including more-than-one-passage cell culture protocols. And yet a further object of the invention is to provide an automated cell culture arrangement comprising different modules such that a tailor-made automated cell culture arrangement can be assembled according to the needs of a particular application and setting. Further objects of the invention include providing specialized tool modules for an automated cell culture arrangement (microscope, centrifuge).

SUMMARY OF THE INVENTION

These objects are met by an automated cell culture arrangement according to independent claims. The dependent claims refer to preferred embodiments.

The automated cell culture arrangement according to the invention comprises at least one closed cell culture module with at least one bioreactor. The closed cell culture module is a closed system, which means that within the closed cell culture module a closed sterile environment can be maintained. The automated cell culture arrangement according to the invention, further comprises at least one pump for pumping liquids within the closed cell culture module and at least one additional tool module, which is configured or configurable to act upon or to monitor the contents of a bioreactor and is movable relative to the at least one closed cell culture module or it is movable relative to one or several components of the at least one closed cell culture module.

The term bioreactor in the context of this application refers to vessels intended for the take-up of cells, which include but are not limited to variations of cell proliferation flasks, centrifugation vessels, cell isolation vessels, cell differentiation vessels, cell seeding vessels, sample vessels, etc.

The relative movement of the at least one closed cell culture module with respect to at least one tool module of the automated cell culture arrangement is possible without opening the at least one closed cell culture module or disconnecting it from the arrangement. Relative movement between a tool module, and the at least one closed cell culture module means that either a tool module or a cell culture module and/or components of either module or both modules are movable in a way, which alters their relative positioning and thereby allows a tool module to act upon or to monitor several bioreactors or their contents of the at least one closed cell culture module.

In the context of this application, the term "tool module" refers to any tool or instrument, which manipulates or monitors in any way anyone or more than one of the components of the cell culture arrangement such as the cell cultures grown in bioreactors of the cell culture arrangement or other components, which are comprised in the cell culture arrangement such as culture media and enzymes etc. Such tool modules include monitoring tool modules for monitoring the process and the cell cultures in the bioreactors, such monitoring modules being, a cell imaging device (e.g. comprising a microscope and a camera), or any kind of sensor technology device such as a pH and temperatures sensors etc. Further possible tool modules include manipulator tool modules such as, shakers, peristaltic pumps, actuators for opening and closing valves, actuators or moving mechanisms for displacing modules or other components of the closed cell culture module and/or the tool modules relative to each other. Yet further tools include harvesting modules such as a cell wash/cell concentration device (e.g. a centrifuge). In preferred embodiments of the closed cell culture module, each one of them comprises a peristaltic pump.

The automated cell culture arrangement according to the invention comprises a plurality of tool modules. Depending on the type of cell culture process required, various preferable embodiments of the arrangement are equipped with variable combinations of tool modules. All arrangements comprise at least one pump for pumping the liquids within the at least one closed cell culture module. Depending on the purpose of the cell culture and demands of the growth protocols, the automated cell culture arrangement includes among the tool modules one or more monitoring tool modules and optionally one or more manipulator tool modules and/or one or more harvesting tool modules or other tool modules such as a fluid pre-heaters tool module. It is at the core of the current invention that of these modules in addition to the at least one pump, at least one of these additional tool modules is movable relative to the closed cell culture module or its components.

Most of the preferred embodiments of the automate cell culture arrangements according to the invention also include valves as components of the closed cell culture module and valve actuators, which can be regarded as tool modules. However and just as a matter of clarity, it is explicitly noted, that mere manipulation of an individual valve by an individual valve actuator for opening and closing a valve does not qualify as an action upon or as a monitoring the contents of a bioreactor.

In the state of the art closed cell culture systems with pumps are known. Such pumps are often peristaltic pumps. During their operation components of the pump are movable relative to the tubing of the closed cell culture module. In some closed cell culture systems liquids such as media, or solutions with enzymes or growth factors etc as well as contents of a bioreactor such as cell based products or cells are pumped through the closed cell culture system. However the automated closed cell culture arrangement according to the invention goes far beyond the level of automation of known automated cell culture systems as described above, because the automated cell culture arrangement according to the invention provides additional tool modules, at least one of which is capable of automatically acting upon or monitoring a bioreactor or its contents, and which is movable relative to the closed cell culture module or its components.

It is a big advantage of the automated cell culture arrangement that thereby a much higher degree of automation and a much higher degree of freedom in the selection of applications according to the requirements of different cell culture growth protocols is achieved. It is a further big advantage that in different embodiments the numbers and configurations of the various tool and cell culture modules can be adapted according to the requirements of particular cell culture protocols, the production volumes, numbers and the frequency of the production etc. In short, a user has many options to configure the automated cell culture arrangement according to the requirements of his or her particular applications.

These much higher degrees of flexibility and of automation compared to automated cell culture systems available in the state of the art are largely based on the shared and automatic use of movable tools, such as microscopes, sensors, centrifuges etc., which without disrupting the closed system of the closed cell culture module act upon or monitor different bioreactors or their contents automatically. In one aspect of the invention such tools are adapted for their application in the automated cell culture arrangement as described below.

In some preferred embodiments, altering the position of a tool module may serve its acting upon or monitoring a different bioreactor of the same or of another closed cell culture system or altering the position of a tool module may serve its acting upon or monitoring the same bioreactor at another point in time. For example, in preferred embodiments of the invention acting upon or monitoring the contents of a bioreactor includes but is not limited to observation growth of a cell culture by microscope and/or camera, monitoring by sensors for pH and/or other parameters including measurement of cell-based products or byproducts, harvesting cells, etc. In one preferred embodiment, a microscope, which is movable to different bioreactors of the same or a closed cell culture automatically can monitor cell growth in a large number of bioreactors. In further preferred embodiments, the moving of a tool module into an altered position may serve its movement from a park in an operating position for observation or action upon the contents of a bioreactor of the at least one closed cell culture module.

In preferred embodiments of the automated cell culture arrangement, the at least one closed cell culture module comprises a manifold, interconnecting tubing and a plurality of valves connecting a plurality of vessels, forming a closed system and further comprising a pump suitable for pumping process fluids and cell culture fluids within the closed cell culture module. In preferred variants of these embodiments a separate peristaltic pump is provided for each closed cell culture system. In preferred embodiments individual vessels of the closed cell culture system are preferably movable both with respect to one another and with respect to various tools for manipulation, observation, thermal treatment, irradiation etc. while the system remains closed.

In preferred embodiments of the automated cell culture arrangements the automated cell culture arrangement comprises at least two units, a cell maintenance unit for proper storage of cell cultivation intermediates, final products as well as for storage of process fluids and a processing unit (or cell processing unit) for cell growth and cell processing. In further preferred embodiments the automated cell culture arrangement optionally comprises additional units, for example an additional storage unit such as for the cryopreservation of cells. In each unit the ambient physical conditions are adjustable individually such as for example temperature and humidity. For example the temperature is regulated to set the processing unit e.g. at a temperature of 37° C., the cell maintenance unit at a temperature of 4° C. and a storage unit at a temperature of −196° C. etc. The automated cell culture arrangement is reconfigurable to place the one or more closed cell culture module entirely or partly within a predetermined unit of the cell culture arrangement and/or to place the one or more tool module entirely or partly within a predetermined unit of the cell culture arrangement. It is within the spirit of the invention to provide automated cell culture arrangements, in which this configuration is selected and fixed for many cell culture cycles or is variably selected and reconfigured for different automated cell culture protocols or even within a running cell culture cycle.

The plurality of vessels, which are part of the closed cell culture module, include one or more flasks for the proliferation of cells, which are preferably kept in the cell processing unit and one or more medium storage flasks, which are preferably kept in the cell maintenance unit. Preferred embodiments include further bioreactors such as centrifugation vessels, cell isolation vessels, sample vials, cell differentiation vessels and other vessels such as medium storage flasks and others wherein some of the vessels are kept in the cell maintenance unit and some of the vessels are kept in the cell processing unit and some of the vessels are kept in either unit depending on the content of the vessel, the cell culture protocol or a particular step of the cell culture protocol.

A preferred embodiment of the cell maintenance unit provides standard refrigerator temperatures to allow proper storage of temperature sensitive liquids such as culture media or enzyme solutions as well as preservation of final cell-based products or cell intermediates such as samples for quality control purposes. Usually those components of the closed cell culture system requiring refrigerated temperatures will be housed in the cell maintenance unit.

In embodiments of the automated cell culture arrangement with a cell processing unit and a cell maintenance unit, preferred variants comprise a housing, in which the at least one cell processing unit and the least one cell maintenance unit are preferably adjacent to each other. The cell processing unit and the cell maintenance unit are separated by an insulating separation wall element, which comprises openings or channels for the passage of the interconnecting tubings, which are part of the at least one closed cell culture module and which connect components of the closed cell culture module, which are located in the cell maintenance unit with components, which are located in the cell processing unit. In preferred variants the openings or channels connecting the processing with the maintenance units comprise insulating material such as foamed polystyrene, through which the tubings are lead. In further preferred embodiments the tubings are positioned as a collection into an opening or channel in the insulating separation wall element. For easy placement and removal of the collection of tubings one or more openings or channels for collections of tubings are preferably positioned at an easily accessible location at an edge of the wall element such as the front edge by the front door of the automated cell culture arrangement.

Preferred embodiments of the housing are designed leak tight and made of appropriate material such that they can be sterilized with hydrogen peroxide vapor.

In preferred embodiments of the automated cell culture arrangement with a cell processing unit and a cell maintenance unit the components of the closed cell culture module, which are arranged within the cell processing unit, are preferably carried by a cell processing rack, and those components, which are arranged within the cell maintenance unit are preferably carried by a cell maintenance rack. The components are configured within the cell maintenance unit or the cell processing unit according to their requirements of the ambient physical conditions. In preferred variants of the cell maintenance rack and the cell processing rack they are mechanically connected or connectable to each other. In preferred variants of racks with a physical connection of the cell maintenance rack and the cell processing rack, the connection comprises a insulating wall element between the cell maintenance rack and the cell processing rack.

Preferred embodiments of the cell maintenance rack for the automated cell culture arrangement accommodate one or more process fluid flasks and/or bags, process sample vials and/or bags, and tubing, as part of the closed cell culture module. In further preferred embodiments of the cell maintenance rack it also accommodates disposable fluid valves as part of the closed cell culture module. Further preferred embodiments of the cell maintenance rack comprise actuators to actuate the fluid valves while in other preferred embodiments actuators for the valves are discrete elements within the cell maintenance unit. The cell maintenance rack can also serve as support structure for tool modules or parts of tool modules and/or actuators including but not limited to cell imaging device, cell wash and collection device, shakers, pumps, valve actuators, grippers, fluid pre-heaters, sensors. The cell maintenance rack is connected to the housing through an electrical and/or a mechanical and/or an optical interface. In preferred variants the interfaces get connected automatically upon insertion of the cell maintenance rack into the housing.

Preferred embodiments of the cell processing rack for the automated cell culture arrangement accommodate mounts for the installation of the closed cell culture module or components. The cell processing rack, which preferably fits into the cell processing unit of the housing is removable from the housing for easier installation of the cell culture module, for cleaning and service purposes etc. Preferred embodiments of the cell processing rack can also serve as support structure for tool modules like cell imaging device, cell wash and collection device, shakers, pumps, valve actuators, grippers, fluid pre-heaters, sensors and/or actuators. In preferred variants the cell processing rack is connected to the housing through an electrical and/or a mechanical and/or an optical interface, which automatically get connected during insertion of the cell processing rack into the housing.

Further preferred embodiments of the automated cell culture arrangement comprise a removable bioreactor holder, which is capable to accommodate different bioreactor vessels of variable formats, such as for example vessels for the cell isolation, cell proliferation and cell differentiation processes. Preferably the bioreactor holder is reversibly attached to the cell processing rack or a surface of the housing of the automated cell culture arrangement. Preferably, this attachment provides directly for flexibility to allow a mechanical movement of the bioreactor holder such as tilting, shaking or lifting. In further embodiments the bioreactor holder includes one or more bioreactor mountings. In preferred embodiments the bioreactor mounting is tiltable by means of a tilting mechanism. The tilted position improves draining of the bioreactors and thereby helps to reduce cell loss. Repeated tilting provides a rocking or shaking mechanism, which for example can be used to distribute cells evenly in the bioreactor vessel or to support enzymatic release of cells grown on tissue cell culture plastics.

Further preferred variants of the bioreactor holder are adjustable in height in order to align a particular bioreactor vessel with a tool module like a cell imaging device or a sensor readout station.

In preferred variants of the bioreactor holder it is designed in a way that installed bioreactor vessels can be gripped and transported e.g. to a cell imaging device and/or sensor readout station by a transport mechanism.

In further preferred variants of the bioreactor holder it has one or more recesses and/or holes, which make certain areas of a bioreactor vessel accessible for optical inspection by a cell imaging device. A cell imaging device can be positioned below and/or above the bioreactor vessels in such a way that pictures from the cells can be taken to assess cell confluence by automated image analysis.

Further preferred variants of the bioreactor holder are part of the cell processing rack, other preferred variants of the bioreactor holder are a discrete part within the cell processing unit.

Various preferred embodiments of the cell culture arrangement are configured by the user in such a way to adapt to variable requirements stipulated by for example a specific cell culture protocol, the number of closed cell culture modules in the cell culture arrangement, the volume of the cell culture vessels etc.

In further preferred embodiments of the cell culture arrangement, the variable configuration includes the stacking of multiple cell maintenance racks and/or cell processing racks. The housing for such an automated cell culture arrangement preferably includes a dedicated space for a movable carrier such as an elevator shaft for an elevator. Preferably the housing further contains guide bars or rail elements along which the movable carrier or the tool element is moved. In preferred embodiments, the elevator is capable of lifting tool modules such as actuators, a cell imaging tool module, cell wash and collection device, pumps, valve actuators, grippers, sensors etc. up and down and positions them at each individual cell maintenance rack and/or cell processing rack when needed during the cell cultivation process for execution of a dedicated operation. This allows tool modules to be shared among several closed cell culture modules, each of which is preferably configured on a cell maintenance rack and/or a cell processing rack.

In further preferred variants two or more closed cell culture modules, are arranged in other spatial arrangements such as horizontal arrangements with a lateral including also circular placement of closed cell culture modules and in further variants additionally stacked vertically, with the closed cell culture modules sharing at least one movable tool modules. In preferred variants the closed cell culture modules, tool and/or components thereof are being moved for example by a movable carrier on rail elements such as guide bars providing for relative lateral or circular movement.

In a preferred embodiment of the invention the manifold is connected to a centrifugation vessel, the centrifugation vessel being arranged in a centrifuge or being automatically transferable, while remaining connected (that is, in liquid connection) to the manifold, for centrifugation in a centrifuge. In preferred variants the transfer of the vessel is effected by means of a centrifuge manipulation device, i.e. a general purpose or dedicated robot manipulator with limited degrees of freedom.

In a further preferred embodiment of the invention, the centrifuge is automatically displaceable along at least one axis within the automated cell culture arrangement, e.g. by means of one or more software controlled drives. This allows to conserve space by moving the centrifuge into an operating position when it is needed, and moving other tools such as a microscope or grippers out of the way. Conversely, when the centrifuge is not in operation, it is moved into a standby position, e.g. at the periphery of the volume inside the arrangement, leaving room for other tools. For example, moving the centrifuge into a park position during downtime allows the centrifuge and the microscope to share space and contributes to an overall space-saving design of the housing. The centrifuge can be part of the cell processing rack or it can be a discrete part within the cell processing unit.

In a preferred embodiment of the invention, the centrifugation vessel is connected to the manifold by means of a rotating coupling, which allows the centrifugation vessel to rotate relative to a conduit linking the vessel to the manifold, without disconnecting the (fluid) link between the centrifugation vessel and the manifold, and without opening the closed cell culture module. This centrifuge thus allows sedimentation of cells within a dedicated cell wash vessel while maintaining the aseptic connection of the cell wash vessel to the remaining cell culture module. The combination of the centrifuge with a robotic pipette device (described below) may be called "cell wash and cell concentration device".

In a preferred embodiment of the invention, a robotic pipette device is disclosed, which allows to effect the most critical handling steps during filling and draining of a centrifugation vessel using a pipette, which is integrated into the centrifugation vessel in an axial manner. Said robotic pipette device preferably comprises two separate mechanisms. A first mechanism is connected to the external part of the pipette. This first mechanism is mechanically configured to lift and to countersink the pipette, and thereby allows adjusting the position of a pipette relative to the fluid level in the centrifugation vessel.

The second mechanism adjusts the inclination of a centrifugation vessel during filling and draining of said centrifugation vessel. After cell centrifugation the supernatant in the centrifugation vessel needs to be carefully removed while leaving the pelleted cells unaffected at the bottom of the vial. This is achieved by countersinking the pipette via said first mechanism, and inclining the centrifugation vessel via said second mechanism and removing the liquid from the centrifugation vessel via the pipette using a pump. The vertical movement of the pipette, inclination of the centrifugation vessel and removing of the liquid occurs in a simultaneous and coordinated manner. Said coordination can either be accomplished by mechanical coupling or by software/sensor based open loop or closed loop control, or a combination thereof. A sensor may be arranged to measure the filling level in the centrifugation vessel, with a controller being configured to control the movement and liquid removal accordingly.

In a preferred embodiment of the invention, a pipette containing element, when extending or retracting the pipette, keeps the pipette from being exposed to the environment outside the closed system of the closed cell culture module, regardless of the position of the pipette relative to the centrifugation vessel While the centrifuge has been presented here in the context of an automated cell culture arrangement, the centrifuge, the centrifuge vessel with rotating with a rotating coupling connected to some tubing and/or the robotic pipette device may also be realized as a stand-alone unit or in combination with other devices not described herein.

In a further preferred embodiment, the automated cell culture arrangement further comprises a valve actuator module, which is movable for activating selected valves of the manifold. The valve actuator module preferably comprises an actuating piece and (linear) actuators for placing the actuating piece in a form fit around a selected valve handle. Rotating the actuation piece with a rotating actuator then operates the valve.

In a preferred embodiment of the invention, a manipulator module being one of the tool modules is configured to selectively move at least one of the tools and of the vessels of the closed cell culture module relative to one another, bringing them into a relative position, in which the tool can be applied to the vessel. The manipulator module preferably comprises a movable gripper configured to grasp and move a selected vessel of the closed cell culture module relative to other vessels of the closed cell culture module. In preferred variants the bioreactor gripper uses vacuum cups, electromagnetic clutches or mechanical clutches to grip bioreactors. The manipulator module can comprise a single serial link manipulator such as a robot arm, which is programmable to move either a tool or a vessel. In an alternative preferred embodiment of the invention, the manipulator module comprises separate actuators for moving both vessels and tools. For example, a tool such as a microscope may be moved along two linear dimensions by means of two actuators, whereas a vessel may be moved along the remaining, third linear dimension by means of a third linear actuator. Working together, these three actuators may bring the tool (microscope) into an operational position relative to a plurality of vessels.

In a further preferred embodiment of the invention, a manipulator module is configured with a tapping mechanism for tapping against a vessel, imparting a slight shock to the vessel, the tapping mechanism preferably being movable together with another tool, such as a gripper or a microscope. Or in a further preferred embodiment a manipulator module is able to perform impacts on bioreactor vessel by abrupt stops of axial moves. This tapping or the abrupt impacts are essentially mimicking the repeated manual tapping of cell culture flasks into the hands of lab technicians. Resulting physical forces support the enzymatic release of cells from the surface of tissue culture plastics or biomaterials where cells were proliferated.

The bioreactor gripper can be part of the cell processing rack or it can be a discrete part within the cell processing unit.

While the manipulator module has been presented here in the context of an automated cell culture arrangement, the manipulator module, and in particular a manipulator module with a gripper and/or a tapping mechanism may also be realized in combination with other devices not described herein.

In a further preferred embodiment of the invention, the automated cell culture arrangement comprises a monitoring tool module being a cell imaging device. The cell imaging device can be a microscope, the microscope comprising a camera and a light source, wherein an optical observation axis is defined by the path of light passing through an object to be observed by the microscope,
a first axis is defined by the path of light passing from the light source before being deflected onto the observation axis,
a second axis is defined by the path of light passing to the camera after being deflected from the observation axis,
and wherein the first and the second axis are at an angle of less than 60 degrees relative to each other.

In other words, the optical path of the microscope, from light source to camera, is preferably folded to be in a pincer-like shape, with two, e.g. approximately parallel, arms reaching around the volume comprising the observed object. The camera and the light source preferably have their optical axes pointing along (essentially) parallel arms of the "pincer", and then being deflected to meet along the observation axis. The optical axis of the light source typically is the optical axis of a collimation lens (system). Further folding of the optical path is possible. The optical path of the microscope is thus deflected to achieve compactness and to save space and weight. The microscope may be tailored for visualization of biological cells grown on 2D surfaces by means of the phase contrast technique.

The entire cell imaging device is preferably movable as one unit, in order to place it in the proximity of a vessel. In a preferred embodiment of the invention, the microscope is movable, by the same actuator or pair of actuators, together with a gripper. The gripper may then comprise a further actuator such that it can reach out, grasp a vessel and move the vessel into the observation volume of the microscope, i.e. the optical path of the microscope.

Software controlled drives are preferably arranged to move the cell imaging device in at least one axis. This allows positioning the cell imaging device at different bioreactors and at different locations of a bioreactor. The cell imaging device can be part of the cell processing rack or it can be a discrete part within the cell processing unit.

In a further preferred embodiment of the invention, the cell imaging device comprises a conventional inverted cell culture microscope or any other (microscope) optics that enables visualization of cells.

In another embodiment of the invention, the cell imaging device preferably comprises a digital camera, which allows capturing images of cells grown on tissue culture plastics or on the surface of any other transparent biomaterial. The digital camera is arranged to capture images through the microscope or through another optical system. Such images can be stored in a database within the housing or in an external database, to which the images are sent. The images can be automatically assessed by a dedicated image analysis software. The results of this image analysis can for example include information about the degree of surfaces covered or not covered by cells, number of cells, cell shape and cell size. Such information can be used for automatic feed back control of the biological process, for example to determine the time point of cell harvest or to select an appropriate bioreactor size for a culture passage.

While the cell imaging device has been presented here in the context of an automated cell culture arrangement, it may also be realized as a stand-alone unit or in combination with other devices not described herein.

In another embodiment of the invention a cell wash/cell concentration device is disclosed, which allows to wash and concentrate cells accordingly when required. Cell wash for example needs to be performed in order to remove harmful enzymes such as trypsin used to release cells following cell proliferation. The concentration of cells for example is conducted when final cells need to be provided within a vial containing large quantities of cells in a small volume of liquid.

The cell wash/cell concentration device consists of at least one specific cell wash vessel as part of the closed cell culture module and a device supporting the concentration of cells in a dedicated liquid volume. The technique used to concentrate cells can be for instance by means of crossflow filtration, and/or by means of using ultrasonic waves to immobilize cells within a fluid flow and/or by means of applying centrifugal forces.

In a further embodiment of this invention a closed cell culture module is disclosed. Said cell culture module consists of at least one cell container or bioreactor connected to a fluid pathway arranged in a way that provides an aseptic self-contained system. Cell containers and/or bioreactors can be described as 3D chambers of various sizes and designs where dedicated process events will be performed and controlled in an automatic manner. Said cell containers and/or bioreactors for example can be a cell isolation vessel, a proliferation vessel, a cell wash vessel, a differentiation vessel, a cell storage vessel and the like. The fluid pathway consists in its simplest form of a single flexible tube connected to an inlet and outlet of a cell container or a bioreactor containing biological cells within a process liquid. By means of a pump for example it will be possible to circulate liquid through the fluid pathway and achieve aeration of the liquid, which maybe critical to maintain metabolic activity of cells. In aspects said basic cell culture module can be successively expanded, e.g. by adding one or more cell containers and/or bioreactors, one or more fluid containers, one or more waste containers, one or more sensors, one or more valves, and/or check valves, one or more manifolds, one or more septums, one or more analytical systems such as a cell counter for example etc. In another aspect of the invention the fluid pathway consisting of flexible tubes will be replaced partially or entirely by a rigid canal system. As a consequence of the modular design of said cell culture module, automation of a great variety of different cell cultivation processes/ protocols as well as cell types will be possible. Users will thus be provided with maximal flexibility and will not be forced changing the scope of an established protocol. For example any user can select between different vessels according to the biological process steps performed (e.g. cell isolation and expansion or expansion over several passages) and connect the selected vessels to the fluid pathway. The different vessels of the cell culture module are easy accessible, which allows any user to manually intervene if desired. Thus it becomes possible to disconnect single elements of the cell culture module during the process, for example a cell sample vial or cell sample bag in case a cell backup is required.

In another embodiment of the invention a cell isolation vessel is disclosed where a tissue biopsy or a cell suspension can be placed in order to deliver the biological input material such as cells or tissue for the process.

In another embodiment of the invention proliferation vessels are disclosed having different surface areas but functionally performing in an equal manner than cell culture T-flasks. These bioreactors are designed to allow proper filling and draining of the cell cultivation area.

In another embodiment of the invention a centrifugation vessel is disclosed, which supports the washing and concentration of cells if operated along with the disclosed centrifuge and the robotic pipette mechanism. The centrifugation vessel is furnished with a dedicated lid holding the pipette, which is positioned in an inclined or parallel orientation relative to the wall of the centrifugation vessel and is bi-directionally moveable in the axial direction of the centrifugation vessel. The pipette is used for filling and draining of the centrifugation vessel by a pump and can be connected to the fluid pathway of the cell culture module. The centrifugation vessel lid is designed in a way that all pipette surfaces that are within the closed cell culture module when the pipette is fully inserted into the centrifugation vessel, are not exposed to the environment when the pipette is moved out of the centrifugation vessel. For this purpose, the centrifugation vessel lid comprises a pipette containing element which keeps the pipette covered regardless of its position. In an embodiment of the invention the pipette is connected to the centrifugation vessel lid with a gaiter or flexible membrane acting as the pipette containing element, which prevents that the outer surface of the pipette is exposed to the environment when the pipette is moved out of the centrifugation vessel. In a further embodiment of the invention, the exposure of the outer surface of the pipette to the environment is prevented by a tube connected to the centrifugation vessel lid and acting as the pipette containing element. The pipette is inserted into and remains within said tube when moved out of the centrifugation vessel. In another embodiment of the invention a cell differentiation or cell seeding vessel is disclosed, which allows cells, which have been concentrated via the cell wash vessel to be seeded onto or within a desired biomaterial and cultivated over a prolonged time period.

DESCRIPTION OF THE PREFERRED EMBODIMENTS

Figure 1:
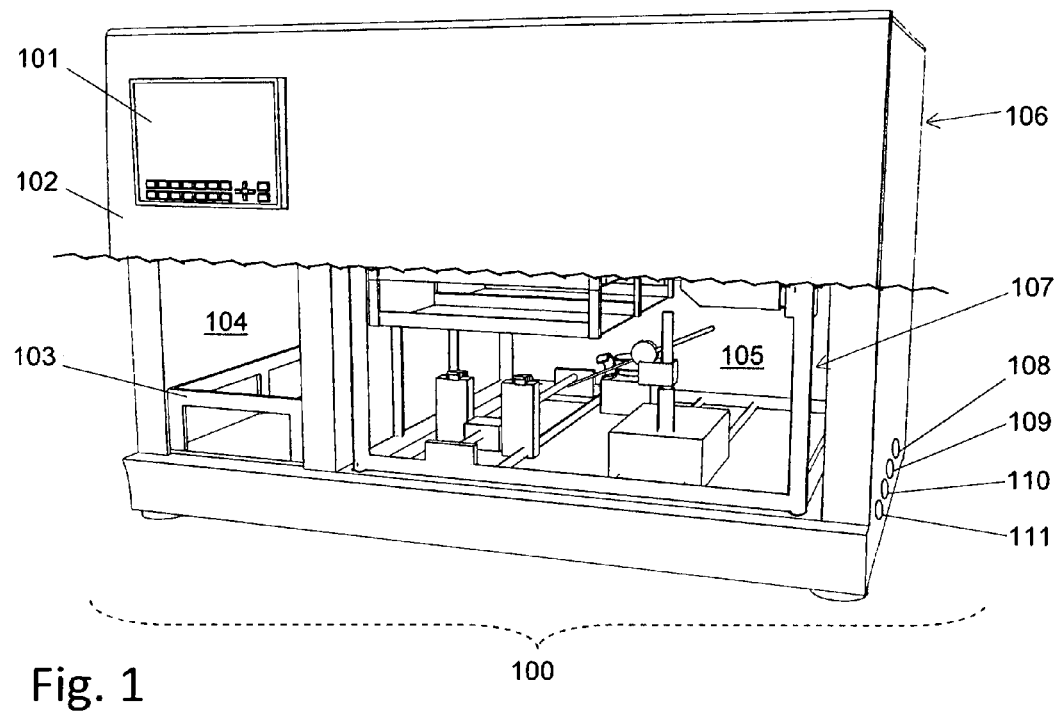
FIG. 1: shows a perspective view of an example of an automated cell culture arrangement with a cell maintenance unit and a cell processing unit.
Figure 2:
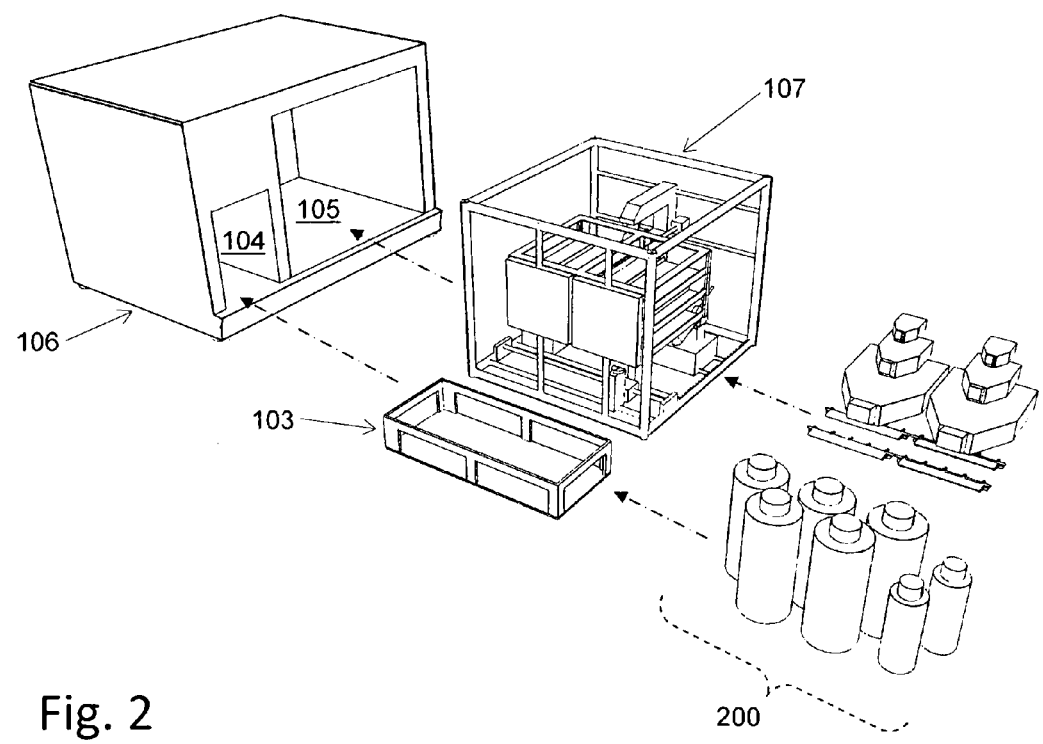
FIG. 2: is an exploded view of the example of the automated cell culture arrangement of FIG. 1.

FIG. 1 and FIG. 2 show an example of an embodiment of an automated cell culture arrangement 100 in a perspective and in an exploded view, respectively. The dimensions of the embodiment as shown are for example about 600 cm in height, 900 cm in width and 600 cm in depth. The automated cell culture arrangement 100 comprises a housing 106, which is separated in a cell maintenance unit 104 and a cell processing unit 105. A housing 100 accommodates at least one cell maintenance rack 103 and at least one cell processing rack 107. The cell processing rack 107 and the cell maintenance rack 103 support the components of a closed cell culture module 200. The cell maintenance unit 104 and the cell processing unit 105 are physically accessible via a door 102.

A user interface 101 is located at the front of the automated cell culture system 100 to provide at least the most critical functions for the operation of the cell culture arrangement. The automated cell culture arrangement comprises also a series of connections such as a connection for power supply 109, a connection for data network 110, a connection for sterilization gas 111, and a connection for $CO_2$ 108.

The cell processing unit 105 of the housing 106 can be regarded as a stand-alone cell culture incubator that provides a standard cell culture environment with respect to $CO_2$ concentration, humidity and temperature. Parameters such as temperature and $CO_2$ partial pressure can be adjusted depending on the requirements of the growth protocol for the cells to be cultivated. The cell processing unit 105 preferably accommodates all or various parts of the components of at the least one closed cell culture module 200. Usually those components of the closed cell culture module 200 requiring standard cell culture conditions such as 37° C., 5% $CO_2$ and humidity will be housed in the cell processing unit 105.

Adjacent to the cell processing unit 105 is the cell maintenance unit 104, which can be regarded as a stand-alone refrigerator. The cell maintenance unit 104 provides standard refrigerator temperatures to allow proper storage of temperature sensitive liquids such as culture media or enzyme solutions as well as preservation of final cell-based products or cell intermediates such as samples for quality control purposes. The cell maintenance unit 104 can accommodate all or various parts of the components of the at least one closed cell culture module 200. Usually those components of the close cell culture module 200 requiring refrigerated temperatures will be housed in the cell maintenance unit 104. In the schematic view of the closed cell culture module as depicted in FIG. 2 only vessels of the closed cell culture module 200 are shown, whereas the manifold with tubing for connecting the vessels and valves etc. are not shown.

Figure 3A:
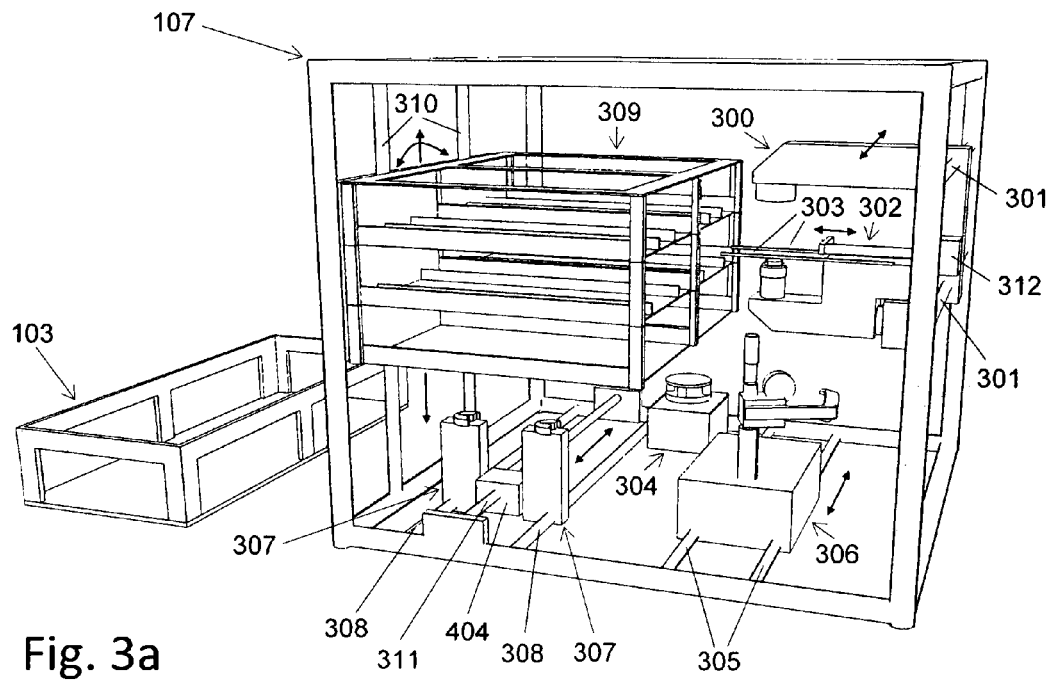
FIG. 3a: shows a perspective view of an example of a cell maintenance rack and a cell processing rack including a bioreactor holder and various tool modules.
Figure 3B:
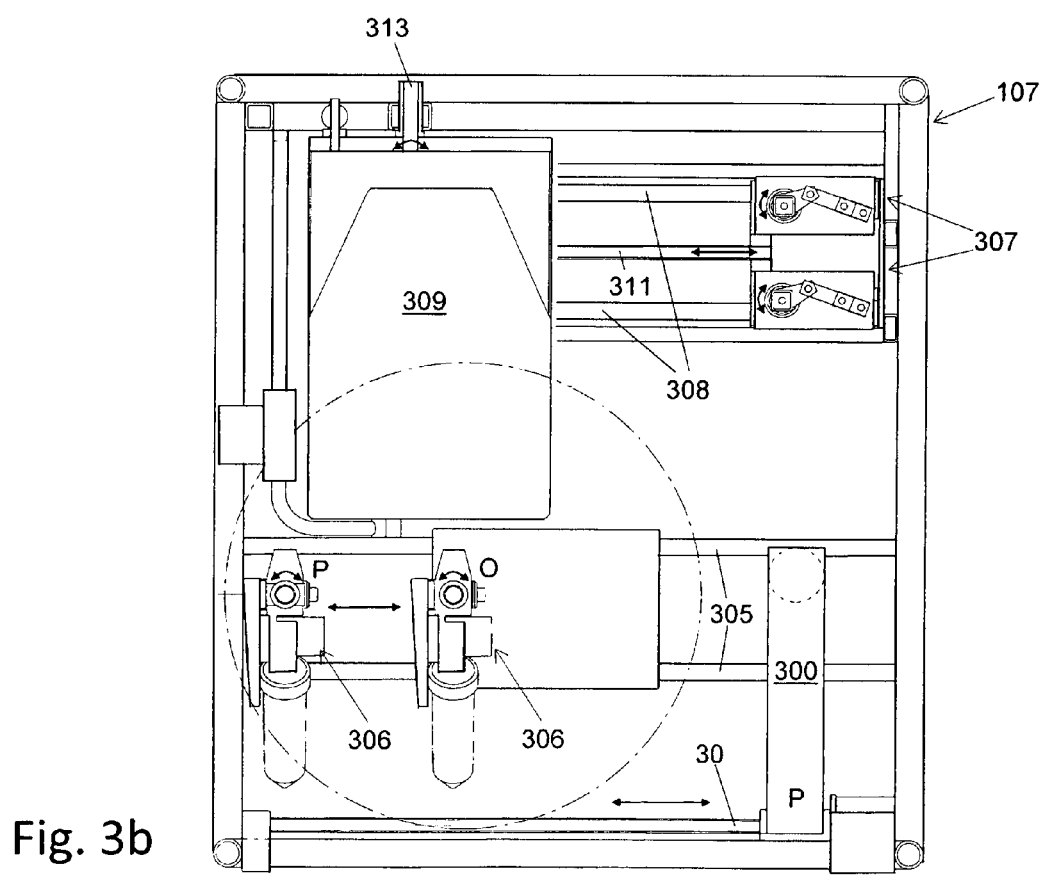
FIG. 3b: shows a top view of an example of a cell processing rack including a bioreactor holder, a cell imaging device and a valve actuator

FIGS. 3a and 3b show a preferred embodiment of a cell processing rack 107 in more detail. In this particular preferred embodiment, the cell processing rack 107 can be regarded as the heart and soul of the automated cell culture arrangement 100: the cell processing rack 107 of FIG. 3a represents an open and accessible support structure, which comprises: a bioreactor holder 309 for holding the close cell culture module or parts of it, a cell imaging device 300 for visualization of biological cells, a cell wash/concentration unit 306 for washing and/or concentration of biological cells, a valve actuator 307 for automated handling of valves integrated into the fluid pathway of the closed cell culture module and a peristaltic pump 304 for transportation of fluid in the closed cell culture module. The cell imaging device 300 can be moved in a horizontal manner (as indicated by the arrows) along to guide bars 301 by means of an electrical drive (not shown). Horizontal movement of the cell imaging device 300 is for example needed to position the cell imaging device in front of a cell proliferation flask to be analyzed located in the bioreactor holder 309. The cell imaging device further carries a bioreactor support structure 303 and a bioreactor gripper 302. The bioreactor support structure 303 allows to position and hold bioreactors or cell culture flasks during visualization at a certain distance to the main components of the cell imaging device 300, e.g. the objective of a microscope. The bioreactor gripper 302 allows to move a cell proliferation flask from the bioreactor holder 309 onto the bioreactor support structure 303 and back. The bioreactor gripper moves forward and backwards as indicated by the arrows in FIG. 3a, by means of an electrical drive 312. The bioreactor holder 309 moves up and down along two guide bars 310 by means of electrical drives (not shown). This vertical adjustment allows to align a certain cell culture flask in the bioreactor holder 309 with the cell imaging device 300. Such an alignment allows the gripper 302 to pull a cell culture flask onto the bioreactor support structure 303 of the cell imaging device 300. An electrical drive (not shown) preferably rotates the bioreactor holder 309 in both directions partially around its longitudinal axis 313 as indicated in FIG. 3b. Repeated partial back and forward rotation of the bioreactor holder results in a shaking effect, which is e.g. needed to evenly distribute cells in cell proliferation flask hold by the bioreactor holder 309. The valve actuator 307 is movable horizontally (as indicated by the arrows in FIG. 3) along two guide bars 308 by means of a thread shaft 311 actuated by an electrical drive 404 (shown in FIG. 4). Horizontal movement of the valve actuator is required to position the valve actuator below the valve, which needs to be actuated. The cell wash/collection device 306, for example a centrifuge, is movable horizontally (as indicated by the arrows) along two guide bars 305, a thread shaft (not shown) and an electrical drive (not shown). FIG. 3b shows for illustration purposes the cell wash/cell collection device 306 twice, once in its operation position O and once in its park position P. When not in use the cell wash/cell collection device 306 is moved into its park position P in order to clear the space for the cell imaging device 300, which is also moveable in horizontal direction. In FIG. 3b, the cell imaging device 300 is shown in its park position (P).

Due to the modular design of the cell processing rack 107 it is possible to disassemble the rack into its single components (cell imaging device such as microscope and camera, bioreactor holder, cell wash/concentration unit such as a centrifuge, bioreactor holder, valve actuator) in order to facilitate cleaning or servicing and exchanging said components in case of failure or for a different cell growth protocol or application. For ease of use during loading of the closed cell culture module and the tool modules to the cell processing rack 107, it can be removed from the cell processing unit 105, either as stand-alone component or in conjunction with the cell maintenance rack 103 being removed at the same time from the cell maintenance unit.

This type of preferred embodiments of the automated cell culture arrangement as described in the FIGS. 1-3b are designed for the use of automated and standardized cultivation of biological cells in vitro including at least the following critical cell culture process steps: isolation of cells out of a tissue biopsy or any other cell source, seeding of cells on planar surfaces or 3D structures for multiplication of cells over one or more passages, release and harvest of cells following expansion, washing and concentration of cells, as well as seeding and growth of cells in various 3D arrangements, which support the generation of de novo tissue.

Figure 4:
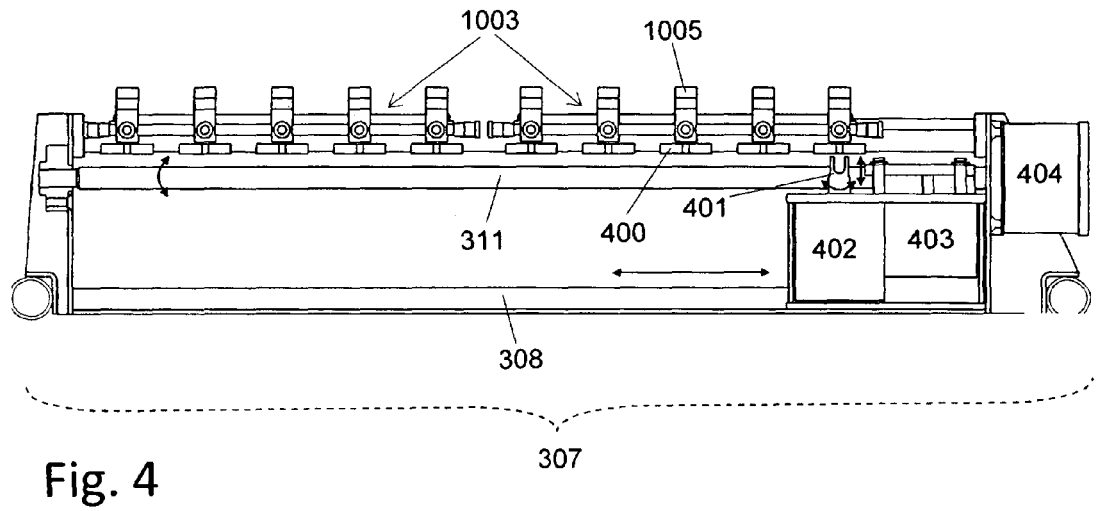
FIG. 4: shows a front view of an example of a valve actuator including a mounted valve manifold.
Figure 5:
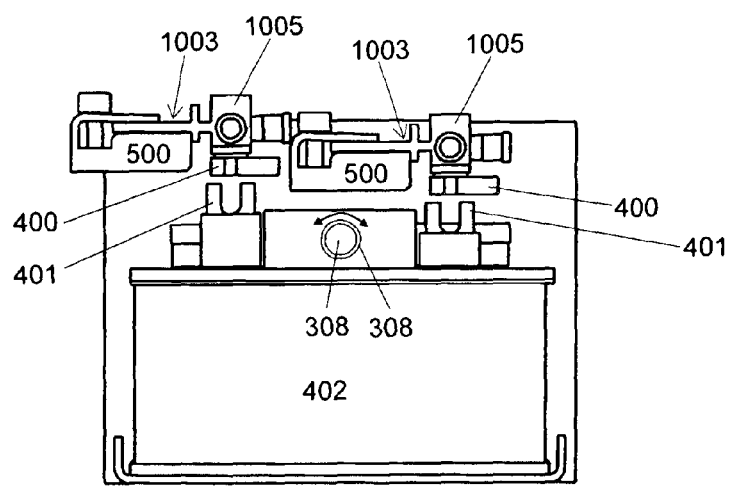
FIG. 5: shows a right side view of an example of a valve actuator including a mounted valve manifold.

FIG. 4 and FIG. 5 show an example of valve actuator in a front view and in a side view, respectively. The purpose of the valve actuator 307 is to actuate, for example, up to twenty 3-way valves, which are preferably arranged in two rows. Each valve 1005 can be set to three different positions by the valve actuator. Changing from one position to the next valve position requires a 90 degree rotation of the valve handle 400. The valve actuator is shown with a mounted valve manifold 1003. A series of 3-way valves 1005 are integrated in the valve manifold 1003. The valve manifold is not part of the valve actuator but it is a discrete part of the closed cell culture module 200. The valve manifold 1003 is clipped to the valve actuator by means of manifold holders 500 shown in FIG. 5. The valve actuator includes two valve handle counterparts 401. The valve handle counterparts 401 can be moved below the valve manifolds 1003 in horizontal direction. The movement is guided by the valve actuator guide bars 308, which are in a parallel orientation to the valve manifold 1003. The electrical drive 404 rotates a thread shaft 311. A female thread turns the rotary movement of the thread shaft 311 into a linear movement of the block consisting of valve handle counter parts 401 and electrical drives 402 and 403. The valve handle counter parts 401 can be vertically moved up via an electrical actuator 402. In its upper position, the valve handle counterpart 401 is engaged with a valve handle 400 of the valve to be actuated. Electrical drive 403 allows to rotate the valve handle counterpart 401 and thereby the valve handle 400 up to, for example, 180 degrees. The two end points of the rotation are determined by mechanical stops. After actuation of a valve the valve handle counterpart 401 is moved down by means of electrical drive 402. In FIGS. 4 and 5, the valve handle counterpart 401 is shown in its lowered position.

Figure 6A:
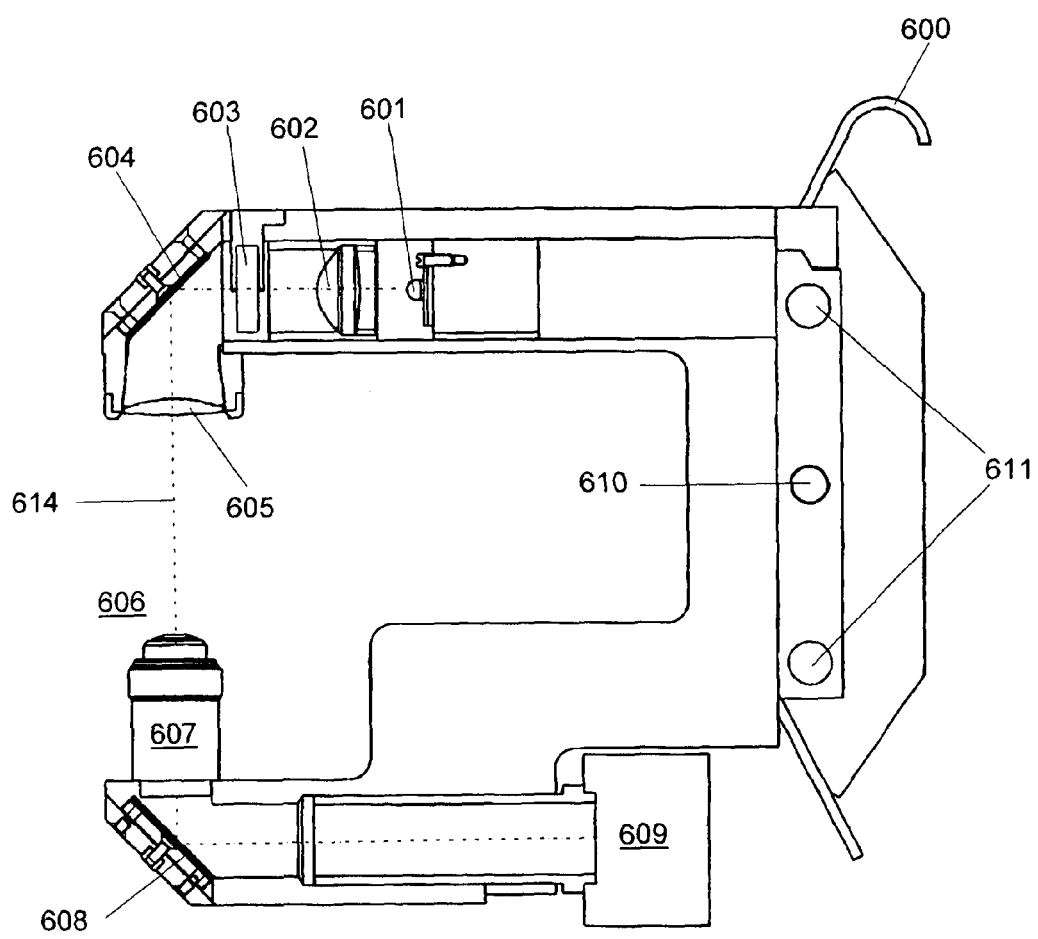
FIG. 6a: shows a right side sectional view of an example of a microscope
Figure 6B:
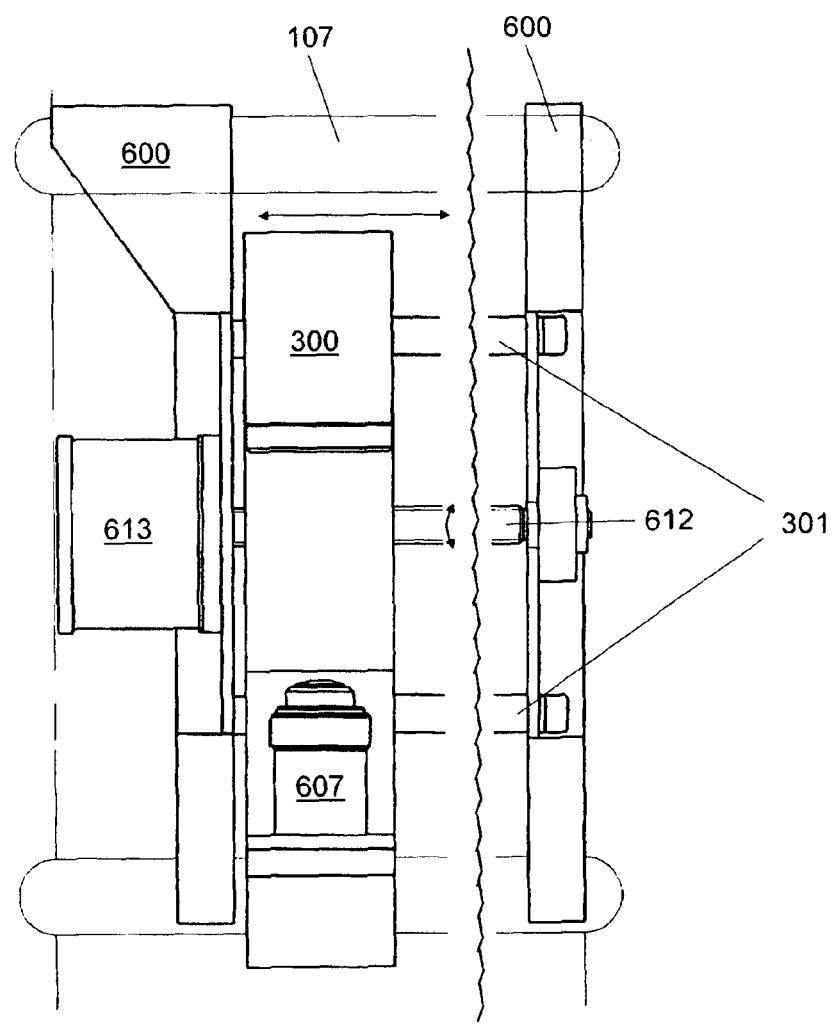
FIG. 6b: shows a front view of an example of a cell imaging device movably attached to a cell processing rack.

FIG. 6a shows a right side sectional view of a cell imaging device and FIG. 6b shows a front view of the same cell imaging device but connected to a cell processing rack. The cell imaging device is in this example a phase contrast microscope with a specially deflected light path. 614. The dimensions of the shown microscope are about 21 cm in height, 8 cm in width and 30 cm in depth. Light emitted by a lamp 601 passes collector lenses 602, subsequently a phase contrast annulus 603. Light passing the phase contrast annulus 603 is deflected by about 90 degrees by a first tilted mirror 604. The specimen to be observed (cell proliferation flask) is positioned in specimen area 606. The light path enters the microscope again via phase contrast object lens 607. The light path is then again deflected by about 90 degrees by a second tilted mirror 608. The microscopical phase contrast image can then be captured by means of a digital camera 609. The hooks 600 allow to hang the cell imaging unit respective microscope into a cell processing rack. FIG. 6b shows the same microscope connected to the frame of a cell processing rack 107. The microscope has in its back end two bore holes 611, in which the guide bars 301 get inserted when the microscope is hooked into the cell processing rack 107. Thread shaft 612 gets inserted into the thread whole 610 if the microscope when connected to the cell processing rack 107. The cell imaging device or microscope can be moved along the two guide bars 301. The electrical drive 613 rotates a thread shaft 612. Female thread 610 turns the rotary movement of the thread shaft 612 into a linear movement of the entire cell imaging device respective the microscope.

Figure 7:
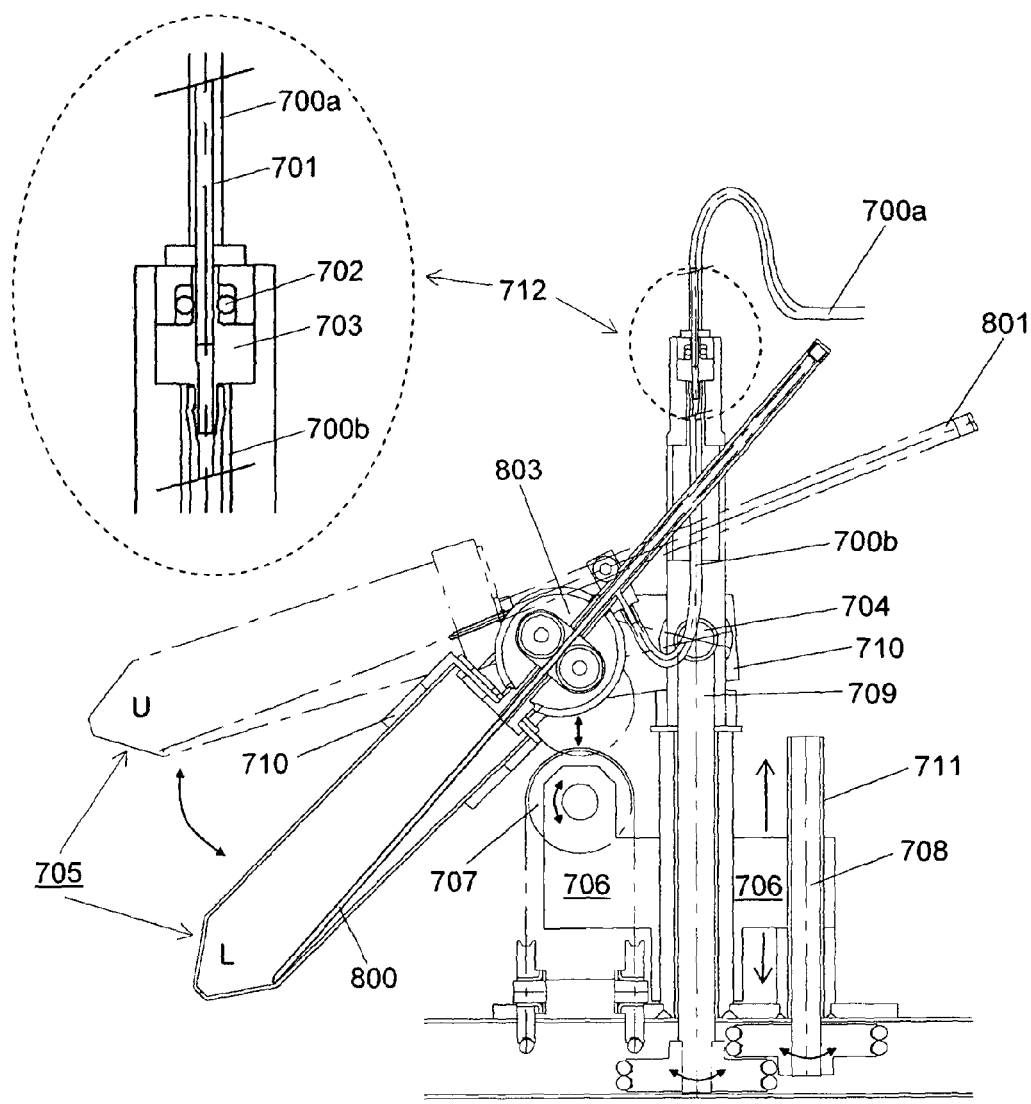
FIG. 7: shows a sectional view of an example of a centrifuge.

FIG. 7 shows a sectional view of cell wash/cell collection device. The cell wash/collection device consists in this example of a centrifuge with a centrifugation vessel inclination mechanism 706 and an installed centrifugation vessel 705. The centrifugation vessel 705 includes an integrated pipette 800 and pipette moving mechanism 803. The centrifugation vessel 705 is also a part of the closed cell culture module 200. The centrifugation vessel 705 is connected to the rest of the closed cell culture module 200 via a connection tube 700a. The centrifugation vessel 705 is held by the centrifugation vessel holder 710. Centrifugation vessel holder 710 is rotatably connected to the centrifugation shaft 709 via a bearing 704. This bearing 704 keeps the inclination angle of the centrifugation vessel holder 710 adjustable. The centrifugation shaft 709 together with the centrifugation vessel holder 710 and the mounted centrifugation vessel 705 are rotated during centrifugation. An electrical drive, which actuates the centrifugation shaft 709 is not shown.

Embroilment of the connecting tube 700a during centrifugation is prevented by tube bearing 712. A stainless steel tube 701 is inserted into the flexible connection tube 700a. The stainless steel tube 701 again is inserted into a Teflon tube connector 703. An O-ring 702 presses the upper thin walled part of the Teflon tube connector 703 against the stainless steel tube 701 and ensures thereby leak tightness of the entire tube bearing 712. The stainless steel tube 701 as well as the connected flexible tube 700a are not rotating during centrifugation, while the Teflon tube connector 703 and the connected flexible tube 700b are rotating together with centrifugation shaft 709, centrifugation vessel holder 710 and centrifugation vessel 705. The tube bearing 712 and the entire centrifugation vessel 705 are part of the closed cell culture module 200. The tube bearing 712 is clipped into the centrifugation shaft 709 during installation of the closed cell culture module in cell a processing rack 107, prior to the start of a biological process.

The centrifugation vessel inclinator 706 and pipette actuator wheel 707 are not used during centrifugation but they are used during filling and draining of the centrifugation vessel 705. The centrifugation vessel inclinator 706 can be vertically moved as indicated by the arrows in FIG. 7. A thread shaft 708 is positioned in thread hole 711 of the centrifugation vessel inclinator 706. Rotation of the thread shaft 708 by an electrical drive (not shown) lifts or countersinks the centrifugation vessel inclinator 706. Lifting of the centrifugation vessel inclinator 706 results, at a certain level, in an engagement of the pipette moving mechanism 803 of the centrifugation vessel 705 with the pipette actuator wheel 707. Further lifting of the centrifugation vessel inclinator 706 changes the inclination angle of the centrifugation vessel 705. (L) and (U) in FIG. 7 indicate two different inclinations of the cell centrifugation vessel 705. Engagement of the pipette moving mechanism 803 with the pipette actuator wheel 707 allows also to sink and countersink the pipette 800 within the centrifugation vessel 705. Rotation of the pipette actuator wheel 707 actuates the pipette moving mechanism 803, which again lowers or lifts the pipette 800. A coordinated actuation of the centrifugation vessel inclinator 706 and the pipette movement mechanism 803 allows to reproduce the movements applied during manual pipetting.

Figure 8:
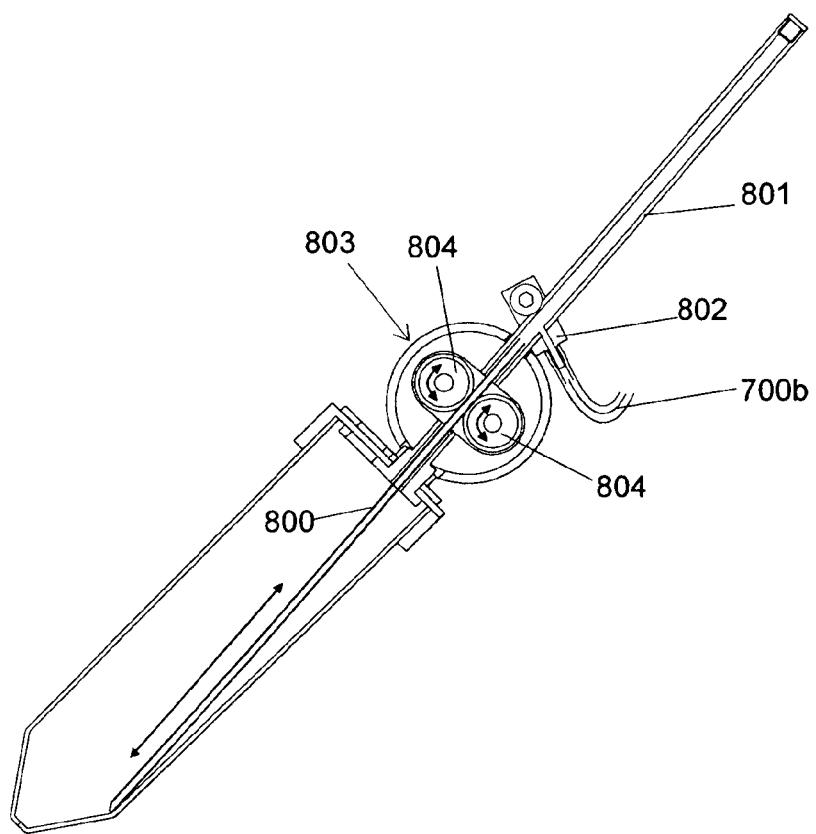
FIG. 8: shows a sectional view of an example of a centrifuge vessel. A tube protects the pipette surfaces from exposure to the environment if pulled out of the centrifugation vessel.

FIG. 8 shows a sectional view of an example of a stand-alone centrifuge vessel. It is the same centrifugation vessel as shown in FIG. 7 with the only difference that it is detached from cell wash/cell collection device. The pipette 800 is clamped between two pipette transport wheels 804 within the pipette movement mechanism 803. Synchronous rotation of the two pipette transport wheel 804 moves the pipette 800 either downwards or upwards as indicated by the arrows. The pipette transport wheels 804 are actuated (details not shown) by the pipette actuator wheel 707 shown in FIG. 7. The pipette 800 gets inserted into the pipette shell 801 when moved upwards. The pipette shell 801 ensures that the pipette is not exposed to the environment and therefore that containment of the closed bioreactor module is not impaired when the pipette is in an extracted position. The tube connector 802 connects the flexible connection tube 700b with the pipette shell 801. Removal or supply of fluid is even possible if the pipette 800 is completely inserted to the pipette shell 801 because there is enough clearance between the outer surface of pipette 800 and the inner surface of the pipette shell 801 in order to allow fluid flow from the flexible tube 700b around and into the pipette 800.

Figure 9:
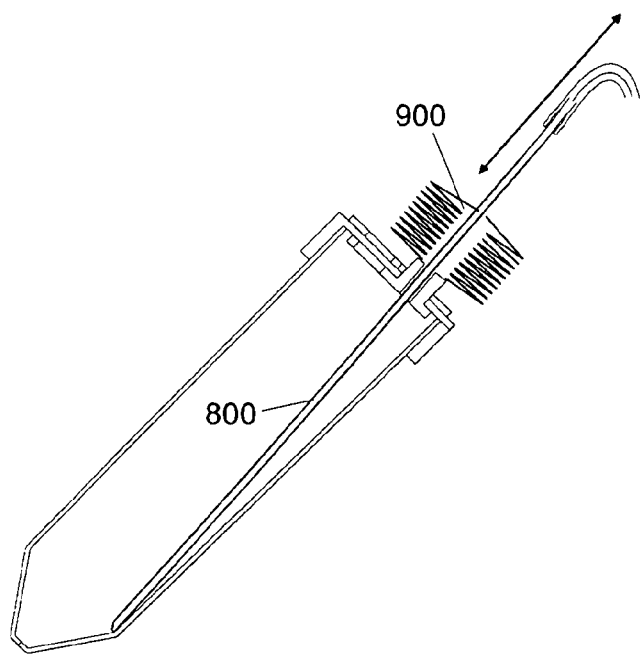
FIG. 9: shows a sectional view of an example of a centrifuge vessel. A gaiter protects the pipette surfaces from exposure to the environment if pulled out of the centrifugation vessel.

FIG. 9 shows a sectional view of a further example of a centrifuge vessel. This version of a centrifugation vessel uses a flexible gaiter to protect the pipette 800 from exposure to the environment when the pipette is moved out of the vessel. The mechanism to move the pipette up- or downwards is not shown. This could be a gripper, which grasps the pipette above the gaiter 900 and which is capable lowering or lifting the pipette as indicated by the arrows. Alternatively, the gaiter arrangement can be combined with a pipette movement mechanism 803 as in the preceding Figure.

Figure 10:
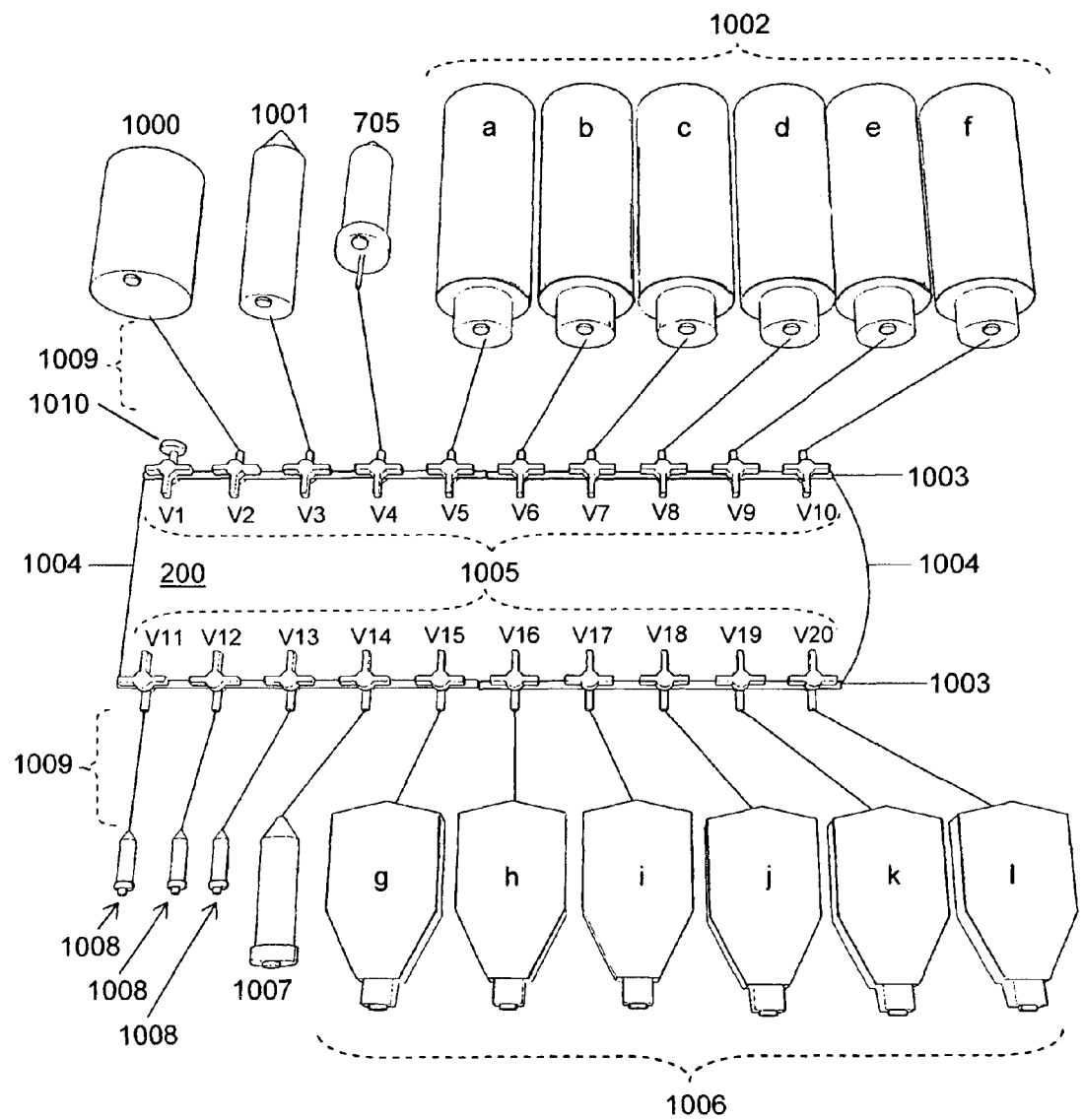
FIG. 10: shows a scheme of an example of a closed cell culture module

FIG. 10 shows a scheme of an example of the closed cell culture module. The entire biological process takes place in the closed cell culture module. Once the cell culture module has been assembled, biological material and process fluids are added and the cell culture module is preferably installed in the cell processing rack 107 and the cell maintenance rack 103. The closed cell culture module is not surrounded by a housing in order to allow visibility and easy access to its different components. The closed cell culture module 200 comprises a fluid circuit and a number of vessels and bioreactors connected to the fluid circuit. The fluid circuit as shown in this particular scheme of FIG. 10 consists of a number of 3-way valves 1005 integrated into two manifold rows 1003, a sterile air filter 1010 connected to one of the valves 1005 and two manifold connection tubes 1004, which connect the two valve manifolds 1003. The sterile air filter 1010 allows to suck air into the pathway and thereby to drain valve manifolds and connecting tubes into a desired vessel. A cell culture module preferably includes but is not limited to some or all of the following vessels/bioreactors: a cell isolation vessel 1007, one or more proliferation bioreactors 1006, a medium conditioning reservoir 1001, one or more sample vials 1008, a centrifugation vessel 705 and differentiation bioreactor 1000. The bioreactors/vessels are connected to the valves 1005 via vessel connection tubes 1009 and couplings (not shown). This setup allows to tailor the closed cell culture module to specific culture approaches, cell types and the type of culture processes to be performed. The process steps, which can be performed in the closed cell culture module include but are not limited to all or some of the following steps: isolation of cells from a biopsy, proliferation of cells, cell harvest, cell washing and concentration, seeding and cultivation of cells on a biomaterial scaffold or membrane. Depending on the steps required for a desired process and according to different user preferences the closed cell culture module is assembled with a variable collection of bioreactors and vessels connected to the basic circuit. For example, the medium storage flasks 1002 can be of different size, depending on the volumes of media required for a particular process. The medium storage flasks 1002 might be filled with solutions like e.g. collagenase, proliferation media, cell detachment media, cell wash solution or a cell storage solution. A preferred embodiment of the cell isolation chamber 1007 comprises a lid including a sterile filter and an in/outlet port at the bottom of the chamber. The chamber has a conical shape to support draining. Tissue needed for cell isolation is placed in the cell isolation vessel prior to the process start. Proliferation flasks 1006 are available in different sizes and selected depending on the number of cells to be proliferated. The sterile air filter as part of the lid allows supply of cells and media in the bioreactor with oxygen and $CO_2$ but also draining and filling of the bioreactor via inlet/outlet port. The inlet/outlet is at the lowest point of the inclined rear wall of the cell proliferation flasks 1006 in order to support draining. The incorporation of a pH and/or $O_2$ sensor (not shown) into the closed cell culture module allows tracking media consumption over time and triggering exchange of media. Parameters like the $O_2$ consumption rate or pH change rate are preferably measured as part of the monitoring of the cell growth within the proliferation bioreactor. The 3D culture bioreactor 1000 will allow to seed cells on to a selected biomaterial e.g. scaffold in order to process or cultivate cells towards a preformed tissue. Obviously, the selection of the kind and number of components forming the closed cell culture module and the arrangement of the components is highly variable for different embodiments according to the invention and FIG. 10 merely discloses one example.

Figure 11:
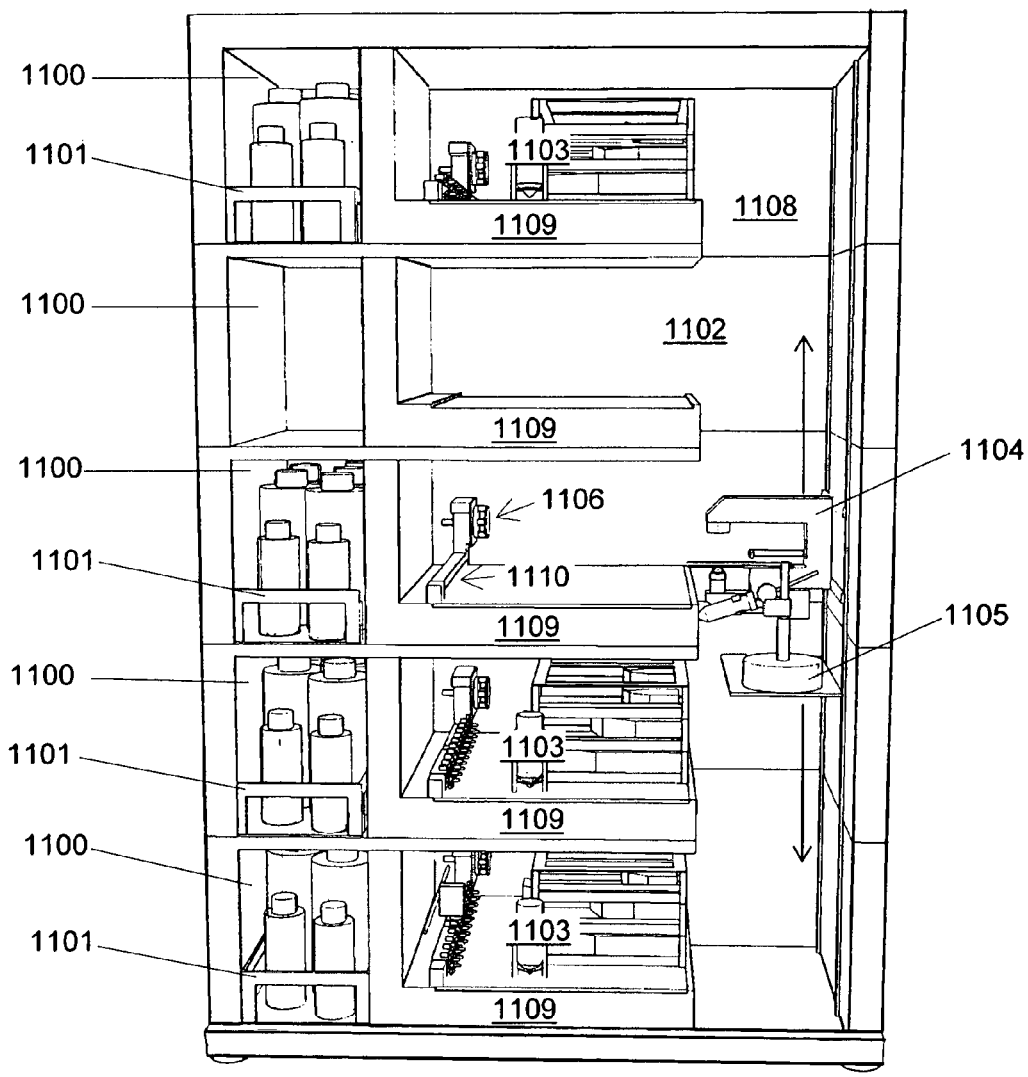
FIG. 11: is a perspective view of an example of a preferred embodiment, with a cell culture arrangement, comprising a housing with a plurality of closed cell culture modules configured on maintenance racks and/or cell processing racks.

FIG. 11 is a perspective view of an example of an automated cell culture arrangement, in which a plurality of individual closed cell culture modules configured on cell maintenance racks 1101 and/or cell processing racks 1109 are accommodated for example by vertical stacking as shown. In this particular example of the automated cell culture arrangement up to 5 individual cell maintenance racks 1101 and/or cell processing racks 1109 can be accommodated. The shown cell culture arrangement is therefore able to run up to 5 independent processes in up to 5 independent closed cell culture modules. Each cell maintenance rack 1101 is located in a separate cell maintenance unit 1100. Preferably, the cell maintenance units 1100 are separated, as shown, however in other embodiments the cell maintenance units are interconnected. Each cell processing rack 1103 has its own level 1109 in the common cell processing unit 1102 space. Peristaltic pumps 1106 and valve actuators 1110 are tools modules, which are frequently used during a biological process. Each cell processing rack 1109 is provided with its own peristaltic pump 1109 and valve actuator 1110. Cell imaging device 1104 and cell wash/concentration device 1105 are not often used during a biological process. One cell imaging device 1104 and one cell wash/concentration device 1105 is sufficient to serve 5 biological processes running parallel. A cell imaging device 1104 and a cell wash/concentration device 1105 are located in an elevator shaft 1101. A movable carrier such as an elevator (not shown) transports the cell imaging device 1104 and the cell wash/concentration device 1105 to each cell processing unit level 1109 and the respective cell processing rack 1103. A software coordinates process steps performed in order to avoid conflicts with respect to the use of the common tool modules located in the elevator shaft. In preferred embodiments the elevator shaft is a predetermined space available in each of the cell processing racks as shown in FIG. 11. In other preferred embodiments the elevator shaft is a predetermined space of the automated cell culture arrangement preferably being within the processing rack of the processing unit of the cell culture arrangement.

Description of Example Process

The following section describes an example of an application of the automated cell culture arrangement performing a cell culture process in an automated manner. The chosen example process includes the isolation of cells from a tissue biopsy, proliferation of these cells, harvest of the proliferated cells, purification and concentration of the harvested cells. This example process shows how the different elements of this invention may be used in a process and how they may interact. However, the automated cell culture arrangement is not at all limited to the described example process but is applicable to a large range of other processes.

Transportation of fluid from one vessel to another vessel in the closed cell culture module 200 requires correct setting of corresponding valves 1005. Setting of the valves by the valve actuator 307 is assumed to be known from standard techniques in the art and not described below.

Process Activities Requiring Manual Handling

Manual Preparation of the Closed Cell Culture Module 200 in a Sterile Environment:

Cell detachment medium is filled into flask 1002c
Proliferation medium is filled into flask 1002d
Cell isolation medium is filled into flask 1002e
Tissue biopsy is put into cell isolation vessel 1007

Manual Installation of the Closed Cell Culture Module 200 on the Cell Processing Rack 107 and the Cell Maintenance Rack 103:

Medium storage flasks 1002 are placed on the cell maintenance rack
Cell proliferation flasks 1006 and cell isolation vessel are fixed on the bioreactor holder 309.
The valve manifold 1003 is installed on the valve actuator 307
A manifold connection tube is connected to the peristaltic pump 304

The Centrifugation vessel is clipped to the centrifugation vessel holder 710 of the cell wash/collection device 306.

Final Preparation of the Automated Cell Culture Arrangement:

The cell processing rack is inserted into the cell processing unit of the housing 106.
The cell maintenance rack is inserted into the cell maintenance unit of the housing 106.
Door 102 of the automated cell culture arrangement is closed.
Process parameters are entered via user interface 101.
Process is started via user interface 101.

Process Activities Performed within the Automated Cell Culture Arrangement

Tissue Biopsy Digest:

Cell isolation medium is pumped from flask 1002e into cell isolation vessel 1007.
Sterile air entering the fluid pathway via sterile filter 1010 is pumped into cell isolation vessel in order to drain the fluid pathway.
Cell isolation vessel is gently agitated by the bioreactor holder 309 for a specified time period. Enzymes contained in the cell isolation medium digest the tissue matrix, whereby the cells get released into the medium.
The cell isolation medium including the suspended cells is pumped from the cell isolation vessel 1007 into the centrifugation vessel 705.

Cell Wash and Cell Concentration Following Tissue Biopsy Digest:

Cell imaging device 300 is moved into park position P and cell wash/collection device 306 is moved into operation position O.
The isolated cells are collected as a pellet in the cone of the centrifugation vessel 705 by centrifugation with cell wash/cell collection device 306.
The supernatant is removed via pipette 800 and pumped into waste flask 1002a. The following elements work in coordinated manner in order to avoid re-suspension and removal of the pelleted cells: Peristaltic pump 304, pipette moving mechanism 803 and centrifugation vessel inclinator 706.
Cell proliferation medium is pumped from the corresponding flask 1002d into the centrifugation vessel 705. The pelleted cells are now re-suspended in the added proliferation medium e.g. by intense back and forward pumping of the proliferation medium and/or by fast up and down movement of the centrifugation vessel inclinator 706.
The washed and suspended cells are pumped from centrifugation vessel 705 into one or several proliferation flasks 1006g (dependent on a specified seeding density to be achieved).

Cell Proliferation (P0):

The cells are homogeneously distributed within the selected proliferation flask(s) 1006g via gently agitating the bioreactor holder 309 for approximately 1 minute.
The cells remain now in the proliferation flask(s) 1006g until they have grown to a pre-defined level of cellular confluence (up to several weeks).
The cell density is analyzed daily by the cell imaging device 300 and the proliferation medium in the proliferation flask is exchanged every 2-3 days by fresh proliferation medium. The medium exchange can occur in regular intervals or it can be triggered by medium properties (e.g. pH value) measured by an integrated sensor.

Cell Density Check During Cell Proliferation:

The cell wash/collection device 306 is moved into its park position P whereas the cell imaging device 300 is moved to a position opposite of the respective cell proliferation flask 1006g to be monitored.

The vertical position of the bioreactor holder 309 is adjusted in a way that the proliferation flask 1006g is aligned with the cell imaging device 300.

The bioreactor gripper grips the proliferation flask 1006g and pulls it on to the bioreactor support of the microscope.

Digital camera 609 captures a microscopical image of the cells inside the proliferation flask 1006g. Cell density is then analyzed by an image analysis software. Pictures at different locations in the flasks can be captured, if the position of the proliferation flask 1006g is changed by the bioreactor gripper 302 and/or by change of the position of the cell imaging device relative to the proliferation flask 1006g.

Medium Exchange During Cell Proliferation:

Used medium is pumped from the selected cell proliferation flask 1006g into waste flask 1002a.

Fresh medium is pumped from the proliferation medium flask 1002d into the proliferation flask 1006g.

Cell Harvest at the End of Cell Proliferation:

Upon achievement of a desired cell density in one or several proliferation flasks, cellular detachment and harvest will occur from the respective proliferation flask(s) 1006g.

The selected proliferation flask 1006g will be emptied by pumping the proliferation medium into the waste flask 1002a.

Cell release medium is now pumped from the cell release medium flask 1002c into proliferation flask 1006g. The enzymes contained in the cell release medium release the cells from the floor of the proliferation flask.

Release of the cells is further supported by some intense impacts caused by the bioreactor gripper 302. The bioreactor gripper 302 grips the proliferation flask and performs a fast acceleration followed by a sudden stop. The course of the cell detachment process is monitored by the cell imaging device 300.

The cells are now suspended in the cell release medium. The cell release medium harms the cells and needs to be removed from the cells as soon as possible. The cell release medium including the cells is therefore transferred into the centrifugation vessel 705.

Cell Wash and Cell Concentration Following Initial Cell Proliferation P0:

The cells are centrifuged and re-suspended in fresh (proliferation) medium by using essentially the same procedure as already explained further above.

Cell Proliferation (P1, P2 Etc.):

Dependent on the number of cells finally required, the cells can now be subjected to additional proliferation cycles. The procedure is essentially the same as described for the initial proliferation cycle P0.

Removal of the Cells from the Automated Cell Culture System:

Following performing the final cell proliferation cycle including cell wash and concentration, the suspended cells are pumped from the centrifugation vessel into a cell storage vessel, which is placed in the refrigerated cell maintenance unit 104. The cells remain in the cell maintenance unit until they are removed from the system by a user.

General remarks: During a process it is always possible to pump a medium sample or cell suspension sample into one of the sample vessels 1008 located in the refrigerated cell maintenance unit. A user can then harvest such a sample vessel by separating it from the closed cell culture module 200 via the use of aseptic connections (not shown). It is also imaginable that said sample vessel 1008 or similar would be the integral part of a second automated device (e.g. cell counter or sterility testing device) to include even cell counting and sterility testing into the described biological process in an automated end to and manner.

LIST OF REFERENCE SIGNS

100 Automated cell culture arrangement
101 User Interface
102 Door (only partly shown)
106 Housing
108 Connection for $CO_2$
109 Connection for power supply
110 Connection for data network
111 Connection for sterilization gas
200 Closed cell culture module
301 Cell imaging unit guide bar
302 Bioreactor gripper
303 Bioreactor support
305 Cell wash/cell concentration device guide bar
306 Cell wash/cell concentration device
307 Valve actuator
308 Valve actuator guide bars
309 Bioreactor holder
310 Bioreactor holder guide bars
311 Threaded shaft for horizontal movement of valve actuator
312 Electrical drive for bioreactor gripper
313 Bioreactor holder longitudinal axis
400 3-way valve handle
401 Valve handle counter part
402 Electrical drive for vertical movement of the valve handle counter part
403 Electrical drive for rotation of valve
404 Electrical drive for horizontal movement of valve actuator
500 Manifold holder
501 Female tread
600 Cell imaging device hook
601 Lamp
602 Collector lens
603 Phase contrast annulus
604 Tilted mirror (Condenser side)
605 Condenser lens
606 Specimen area
607 Phase contrast object lens
608 Tilted mirror (Object lens side)
609 Digital camera
610 Treaded hole
611 Bore hole for guide bar
612 Cell imaging device actuator treaded shaft
613 Electrical drive for horizontal movement of the Cell imaging device
614 light path
701 Stainless steel tube
702 O-ring
703 Teflon tube connector 704 Centrifugation vessel holder bearing
705 Centrifugation vessel
706 Centrifugation vessel inclinator
707 Pipette actuator wheel
708 Centrifugation vessel inclinator thread shaft
709 Centrifuge shaft
710 Centrifugation vessel holder
711 Female tread
712 Tube bearing
800 Pipette
801 Pipette shell
802 Tube connector
803 Pipette moving mechanism
804 Pipette transport wheels
900 Gaiter
1000 Differentiation bioreactor
1001 Medium conditioning reservoirs
1002 Medium storage flasks
1003 Manifold
1004 Manifold connection tube 1005
1005 3-way valve
1006 Cell proliferation flasks
1007 Cell isolation vessel
1008 Sample vessel
1009 Vessel connection tube
1010 Sterile air filter
1100 Cell maintenance unit
1105 Cell wash/collection device
1108 Elevator shaft
1109 Cell processing unit level
1100; 104 Cell maintenance unit
1101; 103 Cell maintenance rack
1102; 105 Cell processing unit
1103; 107 Cell processing rack
1104; 300 Cell imaging device
1106; 304 Peristaltic Pump
1110; 307 Valve actuator
700a Flexible Tube (not rotating)
700b Flexible (rotating)

What is claimed is:

1. An automated cell culture arrangement comprising at least one closed cell culture module comprising at least one bioreactor, the closed cell culture module being a closed system, and a plurality of tool modules comprising at least one pump and at least one additional tool module, wherein at least one of the at least one additional tool module is movable:
relative to the at least one closed cell culture module or relative to one or several components of at the least one closed cell culture module, such that either a tool module or the cell culture module and/or components of either or both modules are movable to alter their relative positioning to allow the tool module to act upon or monitor the at least one bioreactor or their contents,
and configured to act upon or monitor the contents of said at least one bioreactor without opening the closed cell culture module or disconnecting the closed cell culture module from the automated cell culture arrangement;
wherein the cell culture arrangement comprises at least two units, one refrigerated cell maintenance unit that is configured for storage of cell cultivation intermediates, final products, and process fluids and one cell processing unit that is configured for cell growth and cell processing, in which the ambient physical conditions in the different units being adjustable for each unit individually.

2. An automated cell culture arrangement according to claim 1 comprising a movable carrier supporting the movement of the at least one movable tool module relative to the at least one closed cell culture module.

3. The automated cell culture arrangement according to claim 1, wherein the at least one closed cell culture module comprises a manifold, interconnecting tubing and a plurality of valves connecting a plurality of vessels, forming a closed system and wherein each closed cell culture module is configured with a separate set of at least one valve actuator and a pump suitable for pumping process fluids and cell culture fluids within the closed cell culture module.

4. The automated cell culture arrangement according to claim 1, wherein the cell culture arrangement is reconfigurable to place the at least one closed cell culture module and/or the at least one tool module entirely or partly within a predetermined one of the units of the cell culture arrangement.

5. The automated cell culture arrangement according to claim 1, wherein the components of each closed cell culture module are arranged on a cell maintenance rack in the cell maintenance unit and/or on a cell processing rack in the cell processing unit.

6. The automated cell culture arrangement according to claim 5, which comprises two or more closed cell culture modules, each arranged on a cell maintenance and/or a cell processing racks, which racks are being stacked vertically and/or arranged laterally.

7. The automated cell culture arrangement according to claim 6, which comprises two or more closed cell culture modules arranged on cell maintenance and/or cell processing racks, which racks comprise a predetermined space and/or support elements and/or guiding elements for the at least one movable tool element and optionally for the movable carrier for the relative positioning of the at least on tool module relative to the at least one cell culture module.

8. The automated cell culture arrangement according to claim 1, wherein the at least one movable tool module comprises a monitoring module and optionally a manipulator module and/or a harvesting module.

9. The automated cell culture arrangement according to claim 1, wherein a centrifugation vessel is part of the closed cell culture module, the centrifugation vessel being arranged in a centrifuge or being automatically transferable, while remaining connected to the closed cell culture module during centrifugation.

10. The automated cell culture arrangement according to claim 9, wherein the centrifugation vessel is connected to the closed cell culture module by means of a rotating coupling, which allows the centrifugation vessel to rotate relative to a conduit linking the centrifugation vessel to a manifold of the closed cell culture module without disconnecting the link between the centrifugation vessel and the manifold.

11. The automated cell culture arrangement according to claim 10, wherein a robotic pipette device is arranged for filling and draining the centrifugation vessel using a pipette, and wherein the robotic pipette device preferably comprises a first mechanism for extending the pipette into the centrifugation vessel and for retracting the pipette from the centrifugation vessel, and a second mechanism for adjusting the inclination of the centrifugation vessel, the first and second mechanism being configured to move in a coordinated manner during filling and draining of said centrifugation vessel.

12. The automated cell culture arrangement according to claim 11, comprising a pipette containing element which, when extending or retracting the pipette, keeps the pipette from being exposed to the environment outside the closed system of the closed cell culture module, regardless of the position of the pipette relative to the centrifugation vessel.

13. The automated cell culture arrangement according claim 9, wherein the centrifuge is automatically displaceable along at least one axis within the automated cell culture arrangement.

14. The automated cell culture arrangement according to claim 1, comprising a valve actuator module, which is movable for activating selected valves of the manifold.

15. The automated cell culture arrangement according to claim 1, comprising a manipulator module configured to selectively move at least one of the tools and of the vessels of the closed cell culture module relative to one another, bringing them into a relative position, in which the tool can be applied to the vessel, with the manipulator module preferably comprising a movable gripper configured to grasp and move a selected vessel of the closed cell culture module relative to other vessels of the closed cell culture module.

16. The automated cell culture arrangement according to claim 1, comprising a manipulator module with a tapping mechanism configured to tap against a vessel, imparting a shock to the vessel, the tapping mechanism preferably being movable together with another tool.

17. The automated cell culture arrangement according to claim 1, comprising a tool module being a microscope, the microscope comprising a camera and a light source, wherein
an optical observation axis is defined by the path of light passing through an object to be observed by the microscope,
a first axis is defined by the path of light passing from the light source before being deflected onto the observation axis,
a second axis is defined by the path of light passing to the camera after being deflected from the observation axis,
and wherein the first and the second axis are at an angle of less than 60 degrees relative to each other.

18. The automated cell culture arrangement according to claim 15, wherein the movable gripper is attached to and movable with the microscope, and is configured to grasp and move a vessel into the optical path of the microscope.

* * * * *